United States Patent
Crotty et al.

(10) Patent No.: US 6,660,282 B2
(45) Date of Patent: Dec. 9, 2003

(54) SELF FOAMING COSMETIC PRODUCT

(75) Inventors: Brian Andrew Crotty, Branford, CT (US); Craig Stephen Slavtcheff, Guilford, CT (US); Michael Charles Cheney, Fairfield, CT (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 65 days.

(21) Appl. No.: 09/854,373

(22) Filed: May 11, 2001

(65) Prior Publication Data

US 2002/0187103 A1 Dec. 12, 2002

(51) Int. Cl.⁷ .......................... A61K 7/15; A61K 31/74; A61K 7/00
(52) U.S. Cl. ...................... 424/401; 424/73; 424/78.03; 424/400; 514/945
(58) Field of Search .......................... 424/47, 400, 401, 424/70.1, 70.11, 70.16, 70.22, 73, 78.03; 514/945; 510/108, 119, 130, 120, 137

(56) References Cited

U.S. PATENT DOCUMENTS

| | | | |
|---|---|---|---|
| 4,710,374 A | * 12/1987 | Grollier et al. | .............. 132/200 |
| 5,364,031 A | 11/1994 | Taniguchi et al. | |
| 5,635,469 A | 6/1997 | Fowler et al. | |
| 6,030,931 A | 2/2000 | Vinski et al. | |
| 6,087,310 A | * 7/2000 | Henkel | ........................ 510/130 |
| 6,123,934 A | * 9/2000 | Koyama et al. | ......... 424/130.1 |
| 6,251,954 B1 | * 6/2001 | Roulier et al. | ............... 424/401 |

FOREIGN PATENT DOCUMENTS

| | | |
|---|---|---|
| WO | 97/13585 | 4/1997 |
| WO | 02/17876 | 3/2002 |

* cited by examiner

*Primary Examiner*—Thurman K. Page
*Assistant Examiner*—Marina Lamm
(74) *Attorney, Agent, or Firm*—Milton L. Honig

(57) ABSTRACT

A foaming cosmetic product is provided packaged in a non-aerosol mechanical dispenser. The dispenser includes a container for holding a liquid composition, a dispensing head with a housing enclosing a pump mechanism and a screen material in the flow path to convert liquid composition into a foam, and a diptube for delivering liquid from the container to the dispensing head. The cosmetic composition is an opaque creamy, relatively non-viscous fluid, the creamy appearance imparted by a latex with suspended polymer particles compatible with the foaming mechanism.

11 Claims, No Drawings

SELF FOAMING COSMETIC PRODUCT

BACKGROUND OF THE INVENTION

1. Field of the Invention

The invention concerns a foaming cosmetic product based upon a cosmetic composition delivered through a non-aerosol dispenser, wherein the dispenser cooperates with the cosmetic composition to generate a mousse quality foam while concurrently imparting moisturization benefits to the skin.

2. The Related Art

Cosmetic compositions in mousse form have certain appeal to consumers. Foremost is the instant foam achieved by the mere press of a button. Aerosol dispensers employing propellants generally provide a satisfactory foam volume. Unfortunately, aerosol products are under attack for environmental reasons. Volatile organics interfere with the earth's ozone layer and contribute to smog in metropolitan areas. Aerosol packages are also relatively costly to assemble. For all these reasons, attention has been recently directed at non-aerosol dispensers.

U.S. Pat. No. 5,635,469 (Fowler et al.) discloses personal cleansing products comprising a foamable liquid composition and a foam-producing non-aerosol dispenser. The compositions include a surfactant, a water soluble cationic or nonionic polymer, a humectant, a water-insoluble emollient and water. The dispenser employs at least two screens through which the composition is blown to generate a foam.

U.S. Pat. No. 5,364,031 (Taniguchi et al.) discloses a foam dispensing system having nozzles including a velocity decreasing structure. The average foam velocity through these structures is controlled to avoid exceeding a given value. Examples are provided of suitable cosmetic products for use with these systems.

U.S. Pat. No. 6,030,931 (Vinski et al.) describes a non-aerosol pump foaming composition free of water insoluble emollients. Transparent systems achieve a luxurious foam generated through use of select amphoteric surfactants and densifying agents.

Delivery of the cosmetic compositions via non-aerosol dispensers has presented many challenges. Additives within these compositions can interfere with foam properties. Certain types of non-aerosol dispensers which operate with porous filters or meshed screens are not tolerant to particulate components or to even modestly viscous compositions.

For aesthetic and marketing reasons, formulators desire to impart a milky visual effect to the compositions. Milkiness is most often accomplished with titanium dioxide, mica or esters such as glycol distearate. The problem with these ingredients is that the inorganic substances generally clog screens which are necessary for generating the foaming effect. Higher molecular weight esters impart too much viscosity to be foamed by dual screen mousse generators.

Other problems with non-aerosol generated foams is that they often lack a dense luxurious character and often do not provide a cushioned afterfeel.

Accordingly, it is an object of the present invention to provide a cosmetic product in mousse form based on a milky formulation.

Another object of the present invention is to provide a cosmetic product in mousse form which is not subject to clogging within the dispensing mechanism.

Still another object of the present invention is to provide a cosmetic product in mousse form having a relatively low viscosity to achieve pumpability yet displaying an excellent cushioned afterfeel.

These and other objects of the present will become more readily apparent from consideration of the summary and detailed description which follows.

SUMMARY OF THE INVENTION

A foaming cosmetic product is provided which includes:
(A) a non-aerosol dispenser having:
  (i) a container for storing a cleansing composition;
  (ii) a dispensing head located on the container having a housing surrounding a pump mechanism and a foam-forming screen material;
  (iii) a diptube communicating between the container and head functioning to fluidly deliver liquid cleansing composition between container and head and being upstream from the screen material; and
(B) the cosmetic composition including:
  (i) from about 0.01 to about 10% by weight of the cosmetic composition of a latex suspending from about 0.1% to about 90% by weight of the latex of a polymer insoluble in the composition; and
  (ii) from about 0.1 to about 10% by weight of at least one anionic surfactant.

DETAILED DESCRIPTION OF THE INVENTION

Now it has been discovered that a creamy appearance can be imparted to the composition by means of a latex. Particles of polymers forming the latex were found not to clog screens of the dispenser nor to inhibit mousse formation or interfere with skin aesthetics of the product foam.

By the term "latex" is meant water or a fluid of essentially equivalent viscosity, suspending a water-insoluble polymer. Amounts of the latex may be present from about 0.01 to about 10%, preferably from about 0.1 to about 5%, optimally from about 0.5 to about 2% by weight of the cosmetic composition. Amount of the water-insoluble polymer may range from about 0.01 to about 90%, preferably from about 0.1 to about 60%, optimally from about 10 to about 50% by weight of the latex.

Average diameters of the dispersed polymer may range from about 0.001 micron to about 120 micron, preferably from about 0.01 micron to about 1 micron, optimally from about 0.1 micron to about 0.5 micron.

Polymers of the latex include the sub categories of homo and copolymer. Moreover, the term "copolymer" includes polymers fashioned from 2 to 6 different monomers in block or random linkage.

Illustrative of copolymers suitable for the latex emulsion are those formed from styrene, alpha-methylstyrene, divinylbenzene, acrylic acid, methacrylic acid, $C_1$–$C_{20}$ esters of acrylic acid or methacrylic acid, acrylamide, methacrylamide, maleic acid, vinyl acetate, crotonic acid, vinyl neodecanoate and butenoic acid. Exemplative of carboxylate type copolymers are the styrene/alkyl acrylate and partially esterified polyacrylic and polymethacrylic salts and free acid forms. Among the foregoing materials are poly (butyl methacrylate), poly(methyl acrylate), poly(methyl methacrylate), poly(acrylic acid/$C_1$–$C_{20}$ alkyl acrylate) and poly(methacrylic acid/$C_1$–$C_{20}$ alkyl methacrylate). These copolymers may be prepared by polymerization of the respective monomers by traditional oil-in-water or water-in-oil emulsion polymerization techniques. Alternatively, a pseudo latex may be prepared by esterification of preformed polymer with $C_1$–$C_{20}$ alkanol.

A variety of techniques well-known in the art can be used to prepare latexes of water-insoluble polymer particles. These include batch, semi-continuous and seeded emulsion polymerization. See the Encyclopedia of Polymer Science and Engineering, Volume 6,1990.

Particularly preferred polymers for the present invention are styrene/acrylate latexes available from the Rohm & Haas Company sold under the trademark Acusol. The latexes are characterized by pH of about 2 to about 3, having approximately 40% solids in water, with particle size of about 0.1 to about 0.5 micron. Specific Acusol® polymers include Acusol® OP301 (styrene/acrylate) polymer, Acusol® OP302 (Styrene/Acrylate/Divinylbenzene Copolymer), Acusol® OP303 (Styrene/Acrylamide Copolymer), Acusol® OP305 (Styrene/PEG-10 Maleate/Nonoxynol-10 Maleate/Acrylate Copolymer) and (Styrene/Acrylate/PEG-10 Dimaleate Copolymer).

Number average molecular weight for polymers according to the present invention may range from about 1,000 to about 1,000,000, preferably from about 2,000 to about 500,000, optimally from about 5,000 to about 20,000.

A further component of cosmetic compositions according to the present invention is that of an anionic surfactant. Illustrative but not limiting examples include the following classes:

(1) Alkyl benzene sulfonates in which the alkyl group contains from 9 to 15 carbon atoms, preferably 11 to 14 carbon atoms in straight chain or branched chain configuration. Especially preferred is a linear alkyl benzene sulfonate containing about 12 carbon atoms in the alkyl chain.

(2) Alkyl sulfates obtained by sulfating an alcohol having 8 to 22 carbon atoms, preferably 12 to 16 carbon atoms. The alkyl sulfates have the formula $ROSO_3^-M^+$ where R is the $C_{8-22}$ alkyl group and M is a mono- and/or divalent cation.

(3) Paraffin sulfonates having 8 to 22 carbon atoms, preferably 12 to 16 carbon atoms, in the alkyl moiety. These surfactants are commercially available as Hostapur SAS from Hoechst Celanese.

(4) Olefin sulfonates having 8 to 22 carbon atoms, preferably 12 to 16 carbon atoms. Most preferred is sodium $C_{14}$–$C_{16}$ olefin sulfonate, available as Bioterge AS 40®

(5) Alkyl ether sulfates derived from an alcohol having 8 to 22 carbon atoms, preferably 12 to 16 carbon atoms, ethoxylated with less than 30, preferably less than 12, moles of ethylene oxide. Most preferred is sodium lauryl ether sulfate formed from 2 moles average ethoxylation, commercially available as Standopol ES-2®.

(6) Alkyl glyceryl ether sulfonates having 8 to 22 carbon atoms, preferably 12 to 16 carbon atoms, in the alkyl moiety.

(7) Fatty acid ester sulfonates of the formula: $R^1CH(SO_3-M+)CO_2R^2$ where $R^1$ is straight or branched alkyl from about $C_8$ to $C_{18}$, preferably $C_{12}$ to $C_{16}$, and $R^2$ is straight or branched alkyl from about $C_1$ to C6, preferably primarily $C_1$, and M+ represents a mono- or divalent cation.

(8) Secondary alcohol sulfates having 6 to 18, preferably 8 to 16 carbon atoms.

(9) Fatty acyl isethionates having from 10 to 22 carbon atoms, with sodium cocoyl isethionate being preferred.

(10) Dialkyl sulfosuccinates wherein the alkyl groups range from 3 to 20 carbon atoms each.

(11) Alkanoyl sarcosinates corresponding to the formula $RCON(CH_3)CH_2CH_2CO_2M$ wherein R is alkyl or alkenyl of about 10 to about 20 carbon atoms and M is a water-soluble cation such as ammonium, sodium, potassium and trialkanolammonium. Most preferred is sodium lauroyl sarcosinate.

Amounts of the anionic surfactant may range from about 0.1 to about 10%, preferably from about 0.5 to about 6%, optimally from about 2 to about 3% by weight of the cosmetic composition. Instances where formulations contain more than one anionic surfactant, it is advantageous to limit the total amount of anionic surfactant to arrange from about 0.1 to about 20%, more preferably from about 1 to about 10% by weight of the cosmetic composition.

Co-surfactants may also be present to aid in the foaming, detergency and mildness properties. Nonionic and amphoteric actives are the preferred co-surfactants. Suitable nonionic surfactants include $C_{10}$–$C_{20}$ fatty alcohol or acid hydrophobes condensed with from 2 to 100 moles of ethylene oxide or propylene oxide per mole of hydrophobe; $C_2$–$C_{10}$ alkyl phenols condensed with from 2 to 20 moles of alkylene oxides; mono- and di-fatty acid esters of ethylene glycol such as ethylene glycol distearate; fatty acid monoglycerides; sorbitan mono- and di-$C_8$–$C_{20}$ fatty acids; and polyoxyethylene sorbitan available as Polysorbate 80 and Tween 80® as well as combinations of any of the above surfactants.

Other useful nonionic surfactants include alkyl polyglycosides, saccharide fatty amides (e.g. methyl gluconamides) as well as long chain tertiary amine oxides. Examples of the latter category are: dimethyldodecylamine oxide, oleyidi(2-hydroxyethyl)amine oxide, dimethyloctylamine oxide, dimethyldecylamine oxide, dimethyltetradecylamine oxide, di(2-hydroxyethyl)tetradecylamine oxide, 3-didodecoxy-2-hydroxypropyldi(3-hydroxypropyl)amine oxide, and dimethylhexadecylamine oxide.

Amounts of the nonionic surfactant may range from about 0.1 to about 40%, preferably from about 0.5 to about 10%, optimally from about 1 to about 5% by weight of the total composition.

Amphoteric surfactants such as betaines may also be employed as co-actives along with the anionic surfactants. Suitable betaines may have the general formula $RN^+(R^1)_2R^2COO^-$ wherein R is a hydrophobic moiety selected from the group consisting of alkyl groups containing from 10 to 22 carbon atoms, preferably from 12 to 18 carbon atoms; alkyl aryl and aryl alkyl groups containing 10 to 22 carbon atoms with a benzene ring being treated as equivalent to about 2 carbon atoms, and similar structures interrupted by amido or ether linkages; each $R^1$ is an alkyl group containing from 1 to 3 carbon atoms; and $R^2$ is an alkylene group containing from 1 to about 6 carbon atoms. Sulfobetaines such as cocoamidopropyl sultaine are also suitable.

Examples of preferred betaines are dodecyl dimethyl betaine, cetyl dimethyl betaine, dodecyl amidopropyldimethyl betaine, tetradecyldimethyl betaine, tetradecylamidopropyidimethyl betaine, and dodecyldimethylammonium hexanoate. Most preferred is cocoamidopropyl betaine available as Tegobetaine F® sold by Th.

Goldschmidt AG of Germany. Amounts of the betaine may range from about 0.05 to about 15%, preferably from about 0.5 to about 10%, optimally from about 2 to about 8% by weight of the cosmetic composition.

Particularly preferred amphoteric surfactants include the alkali, alkaline earth, ammonium and trialkanolammonium salts of cocoamphoacetate, cocoamphopropionate, cocoamphodipropionate and mixtures thereof. Most preferred is sodium cocoamphoacetate available as Miranol HMA from the Rhone Poulenc Corporation. Similar surfactants are also available as Amphotege® from Lonza Inc., Fair Lawn, N.J. While the sodium salt is preferred, other cations can also be employed including lithium, potassium, magnesium and calcium. Amounts of the amphoteric surfactant may range from about 0.1 to about 20%, preferably from about 1 to about 10%, optimally from about 2 to about 6% by weight of the cosmetic composition. When more than one amphoteric surfactant is present, the total amount of amphoteric surfactant may usually range from about 0.1 to about 10%, preferably from about 0.5 to about 8%, optimally from about 1 to about 5% by weight of the cosmetic composition.

Moisturizing ingredients may also be included in compositions of the present invention. Water soluble moisturizers such as polyhydric alcohol-type humectants are particularly preferred. Typical polyhydric alcohols include glycerol (also known as glycerin), polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably glycerin. The amount of humectant may range anywhere from about 0.5 to about 30%, preferably between about 1 and about 15% by weight of the composition.

Preservatives can desirably be incorporated into the cosmetic compositions of this invention to protect against the growth of potentially harmful microorganisms. Suitable traditional preservatives are EDTA salts and alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are iodopropynyl butyl carbamate, phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the composition. Preservatives are preferably employed in amounts ranging from about 0.01% to about 2% by weight of the composition.

Minor adjunct ingredients may be present in the cosmetic compositions. Among them may be vitamins, colorants, fragrances and opacifiers. Each of these substances may range from about 0.05 to about 5%, preferably between about 0.1 and about 3% by weight.

Advantageously, the compositions of the invention may contain a foam densifying agent. Examples of this substance are waxy materials with a melting point greater than 20° C., preferably greater than 40° C. Illustrative are ethoxylated glyceride esters such as PEG 75 soy glycerides sold under the trademark Acconon S 75. Also useful are $C_8$–$C_{12}$ acyl lactylates such as sodium lauroyl lactylate sold as Pationic 138 C® available from the Patterson Chemical Company. Amounts of these agents may range from about 0.1 to about 10%, preferably from about 0.5 to about 5%, optimally from about 1 to about 3% by weight.

Cationic conditioning agents in monomeric and polymeric type are also useful for purposes of this invention. Examples of the polymeric type include: cationic cellulose derivatives, cationic starches, copolymers of a diallyl quaternary ammonium salt and an acryl amide, quaternized vinylpyrrolidone, vinylimidazole polymers, polyglycol amine condensates, quaternized collagen polypeptide, polyethylene imine, cationized silicon polymer (e.g. Amodimethicone), cationic silicon polymers provided in a mixture with other components under the trademark Dow Corning 929 (cationized emulsion), copolymers of adipic acid and dimethylaminohydroxypropyl diethylenetriamine, cationic chitin derivatives, cationized guar gum (e.g. Jaguar C-B-S, Jaguar C-17, Jaguar C-16, etc. manufactured by the Celanese Company), quaternary ammonium salt polymers (e.g. Mirapol A-15, Mirapol AD-1, Mirapol AZ-1, etc., manufactured by the Miranol Divison of the Rhone Poulenc Company). Most preferred is polyquaternium-11 available as Luviquat®) PQ 11 sold by the BASF Corporation.

Examples of monomeric cationic conditioning agents are salts of the general structure:

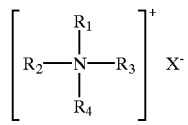

wherein $R^1$ is selected from an alkyl group having from 12 to 22 carbon atoms, or aromatic, aryl or alkaryl groups having from 12 to 22 carbon atoms; $R^2$, $R^3$, and $R^4$ are independently selected from hydrogen, an alkyl group having from 1 to 22 carton atoms, or aromatic, aryl or alkaryl groups having from 12 to 22 carbon atoms; and $X^-$ is an anion selected from chloride, bromide, iodide, acetate, phosphate, nitrate, sulfate, methyl sulfate, ethyl sulfate, tosylate, lactate, citrate, glycolate, and mixtures thereof. Additionally, the alkyl groups can also contain ether linkages, or hydroxy or amino group substituents (e.g., the alkyl groups can contain polyethylene glycol and polypropylene glycol moieties). Preferably the anion is phosphate, especially preferred is hydroxy ethyl cetyl dimonium phosphate available as Luviquat® Mono CP from the BASF Corporation.

Amino silicone quats may similarly be employed. Most preferred is Silquat AD designated by the CTFA as Silicone Quaternium 8, available from Siltech Inc.

Amounts of each cationic agent may range from about 0.05 to about 5%, preferably from about 0.1 to about 3%, optimally from about 0.3 to about 2.5% by weight.

Compositions of this invention are preferably opaque. By the term opaque is meant having less than 20% light transmittance of any wave length in the range of 400 to 700 nm through a sample 1 cm thick.

Compositions of this invention should also be of relatively low viscosity to be pumpable. Viscosity may range from about 1 to about 300 centipoise, preferably from about 3 to about 100 centipoise, optimally from about 5 to about 50 centipoise at 25° C. Measurement is via a Brookfield RVT Viscometer, Spindle No. 1, 100 rpm at 25° C.

Compositions of this invention may have a very broad pH range. Advantageously, the pH will be acidic with pH range from about 2 to about 6.8, preferably from about 3 to about 6, optimally from about 4.5 to about 6 for the total cosmetic composition.

An important element of cosmetic products according to this invention is a non-aerosol mechanical dispenser. The dispenser is generally characterized by a container for storing the composition (preferably a transparent container), a dispensing head defined by a housing containing a pump, and a diptube for transferring the composition from the container into the dispensing head. Foam is created by requiring the composition to pass through a screen material which may be a porous substance such as a sintered material, a wire (plastic or metal) gauze screen or similar structures.

Suitable dispensers are described in U.S. Pat. No. 3,709,437 (Wright), U.S. Pat. No. 3,937,364 (Wright), U.S. Pat. No. 4,022,351 (Wright), U.S. Pat. No. 4,147,306 (Bennett), U.S. Pat. No. 4,184,615 (Wright), U.S. Pat. No. 4,598,862 (Rice), U.S. Pat. No. 4,615,467 (Grogan et al.) and U.S. Pat. No. 5,364,031 (Tamiguchi et al.). Most preferred however is a device sold by the Airspray International Corporation described in WO 97/13585 (Van der Heijden). All these patents are incorporated herein by reference. The Airspray device comprises a container for storing a cleansing composition and a dispensing head, the latter including at least a concentric air pump and liquid pump. Each of the pumps has a piston chamber with a piston displaceable therein and an inlet and discharge, and an operating component for operating the two pumps. The operating component is integral with one of the pistons and comprises an outflow channel with a dispensing opening.

Shut-off mechanisms, rendering it possible to suck up air or liquid, respectively, and dispense them, are present in the inlet and discharge of the pumps. The air pump includes a double-acting shut-off device which can be operated actively by the operating component. The shut-off device prevents both the inlet of air to the air pump and discharge of air therefrom. The air piston is able to be moved freely at least over a small distance with respect to the operating component.

Except in the operating and comparative examples, or where otherwise explicitly indicated, all numbers in this description indicating amounts of material ought to be understood as modified by the word "about".

The term "comprising" is meant not to be limiting to any subsequently stated elements but rather to encompass non-specified elements of major or minor functional importance. In other words the listed steps, elements or options need not be exhaustive.

The following examples will more fully illustrate the embodiments of this invention. All parts, percentages and proportions referred to herein and in the appended claims are by weight unless otherwise indicated.

EXAMPLE 1

A foamable cosmetic product according to the present invention was prepared according to the formula of Table I.

TABLE I

| INGREDIENT | WEIGHT % |
|---|---|
| PHASE A | |
| Water | 68.09 |
| Pationic ® 138A (C) (Sodium Lauryl Lactylate) | 0.50 |
| DL-Panthanol | 0.05 |
| Glycerin | 3.00 |
| Acconon ® S75 (PEG-75 Soy Glycerides) | 1.00 |
| PHASE B | |
| Sodium Lauryl Ether-3 Sulphate (30% Actives) | 6.00 |
| Sodium $C_{14}$–$C_{16}$ Olefin Sulphonate (40% Active) | 6.00 |
| Cocoamidopropyl Betaine (30% Active) | 6.00 |
| Sodium Lauroamphoacetate (32% Active) | 5.00 |

TABLE I-continued

| INGREDIENT | WEIGHT % |
|---|---|
| Polysorbate 80 | 1.00 |
| Mackanate ® DC-30 (Dimethicone Copolyol Sulfosuccinate-30% Active) | 1.66 |
| PHASE C | |
| Polysorbate 20 | 0.15 |
| Fragrance | 0.20 |
| Glydant Plus ® | 0.20 |
| Citric Acid | 0.15 |
| PHASE D | |
| Acusol ® OP301 | 1.00 |

Ingredients of Phase A were charged to a reactor and heated at 60° C. under moderate agitation. Temperature was lowered to 50° C. whereupon ingredients listed under Phase B were singly added one after another allowing sufficient mixing time between each addition.

Temperature was then lowered to 40° C. whereupon the ingredients of Phase C were combined with those of Phase A/B previously formed. Lastly, temperature was lowered to 35° C. and Acusol® OP301 was charged to the remainder of the mixing ingredients.

The resultant cosmetic composition was packaged into an Airspray, double gauze screen dispenser pump package forming the delivery system.

EXAMPLE 2

Another foaming cosmetic product according to the present invention has a formula as described in Table II.

TABLE II

| INGREDIENT | WEIGHT % |
|---|---|
| PHASE A | |
| Water | 73.09 |
| Pationic ® 138A (C) (Sodium Lauryl Lactylate) | 0.50 |
| DL-Panthanol | 0.05 |
| Glycerin | 3.00 |
| Acconon ® S75 (PEG-75 Soy Glycerides) | 1.00 |
| PHASE B | |
| Sodium Lauryl Ether-3 Sulphate (30% Actives) | 4.00 |
| Sodium $C_{14}$–$C_{16}$ Olefin Sulphonate (40% Active) | 4.00 |
| Cocoamidopropyl Betaine (30% Active) | 4.00 |
| Sodium Lauroamphoacetate (32% Active) | 5.00 |
| Plantereen ® 2000 (Alkyl Polyglucoside) | 1.00 |
| Mackanate ® DC-30 (Dimethicone Copolyol Sulfosuccinate-30% Active) | 1.66 |
| PHASE C | |
| Polysorbate 20 | 0.15 |
| Fragrance | 0.20 |
| Glydant Plus ® | 0.20 |
| Citric Acid | 0.15 |
| PHASE D | |
| Acusol ® OP301 | 0.50 |

The composition in Table II is formulated in a manner similar to that found under Example 1. Likewise, the resultant product is placed in an Airspray pump as the dispensing package.

EXAMPLE 3

Another foam producing cosmetic product according to the present invention has a foamable composition described under Table Ill.

TABLE III

| INGREDIENT | % WEIGHT/WEIGHT |
|---|---|
| Lauryldimonium Hydroxypropyl Hydrolyzed Collagen | 7.14 |
| Hexylene Glycol | 6.50 |
| Decyl Polyglucose | 6.00 |
| Sodium Lauryl Ether-3 Sulphate (30% Active) | 6.00 |
| Laurodimonium Hydroxypropyl Oxyethyl Cellulose | 5.67 |
| Cocoamidopropyl Betaine (30% Active) | 5.00 |
| Glycerin | 3.00 |
| Sodium Isostearoyl Lactylate | 1.00 |
| Acusol ® OP 302 | 1.00 |
| Fragrance | 0.35 |
| Glydant Plus ® | 0.10 |
| Tetrasodium EDTA | 0.10 |
| Water | balance |

EXAMPLE 4

Various potential opacifiers were evaluated for their performance characteristics. Table IV lists the base of composition into which were formulated the opacifiers.

TABLE IV

| INGREDIENT | WEIGHT % |
|---|---|
| Water | balance |
| Pationic ® 138C (Na lauroyl lactylate) | 0.50 |
| DL-Panthanol | 0.05 |
| Acconon ® S75 (PEG-75 Soy Glycerides) | 1.00 |
| Glycerin | 5.00 |
| Sodium Lauryl Ether-3 Sulphate (30% Active) | 6.00 |
| Sodium $C_{14}$–$C_{16}$ Olefin Sulphonate (40% Active) | 6.00 |
| Cocoamidopropyl Betaine (30% Active) | 6.00 |
| Sodium Lauroamphoacetate (32% Active) | 8.00 |
| Polysorbate 80 | 1.00 |
| Dimethicone Copolyol Sulfosuccinate (Mackanate ® DC-30) | 1.66 |
| Polysorbate 20 | 0.15 |
| Glydant Plus ® | 0.10 |
| Fragrance | 0.20 |
| Citric Acid | 0.15 |
| Opacifier | * |

TABLE V

| Opacifier | Weight (%) | Effect on Product | Stability |
|---|---|---|---|
| Styrene/Acrylate Copolymer (Acusol ® OP301) | 0.20 | Good white/opaque appearance and creamy rich lather. No apparent drawbacks. | Stable |
| Styrene/Acrylamide Copolymer (Acusol ® OP303) | 0.20 | Good white/opaque appearance and creamy rich lather. No apparent drawbacks. | Stable |
| Styrene/PEG-10 Maleate/Nonoxynol-10 Maleate/Acrylate Copolymer (Acusol ® OP305) | 0.20 | Good white/opaque appearance and creamy rich lather. No apparent drawbacks. | Stable |
| Zinc Oxide | 0.20 | Imparted insufficient opacity to product. | Settled out overnight |
| Ultra Fine Silica | 0.20 | Imparted insufficient opacity to product. | Settled out overnight |
| Ultra Fine Silica | 6.18 | Good white/opaque appearance. Clogged screen of pump. | Settled out overnight |
| Silica | 0.20 | Imparted insufficient opacity to product. | Settled out overnight |
| Silica | 2.22 | Clogged screen of pump. | Settled out overnight |
| Water Dispersible Titanium Dioxide | 0.20 | Left slight white stain on sink and countertop. | Settled out overnight |
| Water Dispersible Titanium Dioxide | 1.65 | Left white stain on sink and countertop. | Settled out overnight |

Inorganic opacifiers such as zinc oxide, silica and titanium dioxide were relatively ineffective at low concentrations (i.e. 0.2%) to impart sufficient opacity to the base composition. Levels of these materials which did sufficiently opacify were unstable in the system and/or clogged the pump screen. By contrast, the Acusol® latexes performed well. Opacity and phase stability were both good. Screens were not clogged and a creamy, rich lather was able to be generated.

The foregoing description and examples illustrate selected embodiments of the present invention. In light thereof variations and modifications will be suggested to one skilled in the art, all of which are within the spirit and purview of this invention.

What is claimed is:

1. A foaming skin cosmetic product comprising:
   (A) a non-aerosol dispenser comprising:
      (i) a container for storing a cosmetic composition;
      (ii) a dispenser head located on the container having a housing surrounding a pump mechanism and a foam-forming screen material;
      (iii) a diptube communicating between the container and head functioning to fluidly deliver liquid cleansing composition between container and head and being upstream from the screen material; and
   (B) the cosmetic composition comprising:
      (i) from about 0.01 to about 10% by weight of the cosmetic composition of a latex suspending from about 0.1% to about 90% by weight of the latex of a polymer insoluble in the composition; and
      (ii) from about 0.1 to about 10% by weight of at least one anionic surfactant.

2. The product according to claim 1 wherein the screen material is a wire gauze.

3. The product according to claim 2 wherein a second wire gauze is placed down stream from a first wire gauze, the cosmetic composition being required to traverse both the first and second wire gauze to achieve a foam.

4. The product according to claim 1 wherein the screen material is a sintered material.

5. The product according to claim 1 wherein the polymer is formed from a monomer selected from the group consisting of styrene, alpha-methylstyrene, divinylbenzene, acrylic acid, methacrylic acid, $C_1$–$C_{20}$ esters of acrylic acid or methacrylic acid, acrylamide, methacrylamide, maleic acid, vinyl acetate, crotonic acid, vinyl neodecanoate and butenoic acid.

6. The product according to claim 1 wherein the polymer is selected from the group consisting of Styrene/Acrylate Copolymer, Styrene/Acrylate/Divinylbenzene Copolymer, Styrene/PEG-10 Maleate/Nonoxynol-10 Maleate/Acrylate Copolymer, Styrene/Acrylamide Copolymer and Styrene/Acrylate/PEG-10 Dimaleate Copolymer.

7. The product according to claim 1 wherein the polymer is a styrene/acrylate copolymer.

8. The product according to claim 1 wherein the latex is present in an amount from about 0.1 to about 5% by weight of the cosmetic composition.

9. The product according to claim 1 wherein the pH ranges from about 2 to about 6.8.

10. The product according to claim 1 wherein all anionic surfactants are present in total amount from about 0.1 to about 20% by weight of the cosmetic composition.

11. A foaming skin cosmetic product comprising:
(A) a non-aerosol dispenser comprising:
  (i) a container for storing a cosmetic composition;
  (ii) a dispenser head located on the container having a housing surrounding a pump mechanism and a foam-forming screen material;
  (iii) a diptube communicating between the container and head functioning to fluidly deliver liquid cleansing composition between container and head and being upstream from the screen material; and
(B) the cosmetic composition comprising:
  (i) from about 0.1 to about 5% by weight of the cosmetic composition of a latex suspending from about 0.1% to about 90% by weight of the latex of a polymer selected from the group consisting of Styrene/Acrylate Copolymer, Styrene/Acrylate/Divinylbenzene Copolymer, Styrene/PEG-10 Maleate/Nonoxynol-10 Maleate/Acrylate Copolymer, Styrene/Acrylamide Copolymer and Styrene/Acrylate/PEG-10 Dimaleate Copolymer; and
  (ii) from about 0.1 to about 10% by weight of at least one anionic surfactant.

* * * * *